US005958083A

United States Patent [19]

Onishi et al.

[11] Patent Number: 5,958,083

[45] Date of Patent: Sep. 28, 1999

[54] PREVENTION OF BACK-STAINING IN STONE WASHING

[75] Inventors: Masahiro Onishi, Chiba, Japan; Merete Fich, Charlottenlund, Denmark; Annette Hanne Toft, Bagsvaerd, Denmark; Martin Schülein, København, Denmark

[73] Assignee: Novo Nordisk A/A, Bagsvaerd, Denmark

[21] Appl. No.: 09/033,537

[22] Filed: Mar. 2, 1998

Related U.S. Application Data

[63] Continuation of application No. PCT/DK96/00364, Sep. 3, 1996.

[30] Foreign Application Priority Data

Sep. 8, 1995 [JP] Japan .................................... 0993/95

[51] Int. Cl.[6] .......................... C11D 3/386; D06M 16/00; C12N 9/42

[52] U.S. Cl. ........................... 8/102; 8/114; 8/115; 8/401; 252/8.91; 252/8.86; 435/209; 435/263

[58] Field of Search ................................ 8/102, 114, 115, 8/401; 252/8.91, 8.86; 435/263, 209

[56] References Cited

U.S. PATENT DOCUMENTS 4,832,864 5/1989 Olson ......................................... 8/102

FOREIGN PATENT DOCUMENTS

| | | |
|---|---|---|
| WO 91/17243 | 11/1991 | WIPO . |
| WO 94/07983 | 4/1994 | WIPO . |
| WO 94/21801 | 9/1994 | WIPO . |
| WO 94/29426 | 12/1994 | WIPO . |
| WO 95/09225 | 4/1995 | WIPO . |
| WO 95/16782 | 6/1995 | WIPO . |
| WO 95/24471 | 9/1995 | WIPO . |

OTHER PUBLICATIONS

Chemical Abstracts, Vo. 121, No. 18, The Abstract No. 207550s, Book Pap., Int. Conf. Exhib. 1992, 243–249. (Month Unknown).

Biochem. J., vol. 280, 1991, Bernard Henrissat, pp. 309–316, Table 1. (Month Unknown).

Biochem. J., vol., 293, 1993, Bernard Henrissat et al., pp. 781–788, Table 1. (Month Unknown).

*Primary Examiner*—Alan Diamond

*Attorney, Agent, or Firm*—Steve T. Zelson, Esq.; Reza Green, Esq.

[57] ABSTRACT

This invention relates to a method of forming localized variation of color density in the surface of a dyed cellulosic fabric, and to a composition for use in the method.

16 Claims, No Drawings

SEQUENCE LISTING

```
(1) GENERAL INFORMATION:

   (iii) NUMBER OF SEQUENCES: 1

(2) INFORMATION FOR SEQ ID NO:1:

     (i) SEQUENCE CHARACTERISTICS:
          (A) LENGTH: 551 amino acids
          (B) TYPE: amino acid
          (C) STRANDEDNESS: single
          (D) TOPOLOGY: linear

    (xi) SEQUENCE DESCRIPTION: SEQ ID NO:1:

Ala Pro Ala Val Pro Phe Gly Gln Leu Lys Val Gln Gly Asn Gln Leu
 1               5                  10                  15

Val Gly Gln Ser Gly Gln Ala Val Gln Leu Val Gly Met Ser Ser His
            20                  25                  30

Gly Leu Gln Trp Tyr Gly Asn Phe Val Asn Lys Ser Ser Leu Gln Trp
        35                  40                  45

Met Arg Asp Asn Trp Gly Ile Asn Val Phe Arg Ala Ala Met Tyr Thr
    50                  55                  60

Ala Glu Asp Gly Tyr Ile Thr Asp Pro Ser Val Lys Asn Lys Val Lys
65                  70                  75                  80

Glu Ala Val Gln Ala Ser Ile Asp Leu Gly Leu Tyr Val Ile Ile Asp
                85                  90                  95

Trp His Ile Leu Ser Asp Gly Asn Pro Asn Thr Tyr Lys Ala Gln Ser
            100                 105                 110

Lys Ala Phe Phe Gln Glu Met Ala Thr Leu Tyr Gly Asn Thr Pro Asn
        115                 120                 125

Val Ile Tyr Glu Ile Ala Asn Glu Pro Asn Gly Asn Val Ser Trp Ala
    130                 135                 140

Asp Val Lys Ser Tyr Ala Glu Glu Val Ile Thr Ala Ile Arg Ala Ile
145                 150                 155                 160

Asp Pro Asp Gly Val Val Ile Val Gly Ser Pro Thr Trp Ser Gln Asp
                165                 170                 175

Ile His Leu Ala Ala Asp Asn Pro Val Ser His Ser Asn Val Met Tyr
            180                 185                 190

Ala Leu His Phe Tyr Ser Gly Thr His Gly Gln Phe Leu Arg Asp Arg
```

-continued

```
        195                 200                 205

Ile Thr Tyr Ala Met Asn Lys Gly Ala Ala Ile Phe Val Thr Glu Trp
    210                 215                 220

Gly Thr Ser Asp Ala Ser Gly Asn Gly Gly Pro Tyr Phe Pro Gln Ser
225                 230                 235                 240

Lys Glu Trp Ile Asp Phe Leu Asn Ala Arg Lys Ile Ser Trp Val Asn
                245                 250                 255

Trp Ser Leu Ala Asp Lys Val Glu Thr Ser Ala Ala Leu Met Pro Gly
            260                 265                 270

Ala Ser Pro Thr Gly Gly Trp Thr Asp Ala Gln Leu Ser Glu Ser Gly
        275                 280                 285

Lys Trp Val Arg Asp Gln Ile Arg Gln Ala Thr Gly Gly Gly Ser Gly
    290                 295                 300

Asn Pro Thr Ala Pro Ala Ala Pro Thr Asn Leu Ser Ala Thr Ala Gly
305                 310                 315                 320

Asn Ala Gln Val Ser Leu Thr Trp Asn Ala Val Ser Gly Ala Thr Ser
                325                 330                 335

Tyr Thr Val Lys Arg Ala Thr Thr Ser Gly Gly Pro Tyr Thr Asn Val
            340                 345                 350

Ala Thr Gly Val Thr Ala Thr Ser Tyr Thr Asn Thr Gly Leu Thr Asn
        355                 360                 365

Gly Thr Thr Tyr Tyr Tyr Val Val Ser Ala Ser Asn Ser Ala Gly Ser
    370                 375                 380

Ser Ala Asn Ser Ala Gln Ala Ser Ala Thr Pro Ala Ser Gly Gly Ala
385                 390                 395                 400

Ser Thr Gly Asn Leu Val Val Gln Tyr Lys Val Gly Asp Thr Ser Ala
                405                 410                 415

Thr Asp Asn Gln Met Lys Pro Ser Phe Asn Ile Lys Asn Asn Gly Thr
            420                 425                 430

Thr Pro Val Asn Leu Ser Gly Leu Lys Leu Arg Tyr Tyr Phe Thr Lys
        435                 440                 445

Asp Gly Thr Ala Asp Met Ser Ala Ser Phe Asp Trp Ala Gln Ile Gly
    450                 455                 460

Ala Ser Asn Val Ser Ala Ala Phe Ala Asn Phe Thr Gly Ser Asn Thr
465                 470                 475                 480

Asp Thr Tyr Val Glu Leu Ser Phe Ser Ala Gly Ser Gly Ser Ile Pro
                485                 490                 495

Ala Gly Gly Gln Thr Gly Asp Ile Gln Leu Arg Met Tyr Lys Thr Asp
            500                 505                 510

Trp Ser Asn Phe Asn Glu Ala Asn Asp Tyr Ser Tyr Asp Gly Ala Lys
        515                 520                 525

Thr Ala Tyr Ala Asp Trp Asn Arg Val Thr Leu His Gln Asn Gly Thr
    530                 535                 540

Leu Val Trp Gly Thr Thr Pro
545                 550
```

PREVENTION OF BACK-STAINING IN STONE WASHING

CROSS-REFERENCE TO RELATED APPLICATIONS

This application is a continuation application of PCT/DK96/00364 filed Sep. 3, 1996 and claims priority under 35 U.S.C. 119 of Danish application 0993/95 filed Sep. 8, 1995, the contents of which are fully incorporated herein by reference.

TECHNICAL FIELD

This invention relates to a method of forming localized variation of color density in the surface of a dyed cellulosic fabric, and to a composition for use in the method.

BACKGROUND ART

In the manufacture of garments from dyed cellulosic fabric, e.g., blue jeans from indigo-dyed denim, it is common to treat the denim so as to provide a "stone-washed" look (localized abrasion of the color in the denim surface). This can be achieved by agitating the denim in an aqueous medium containing a mechanical abrasion agent such as pumice, an abrading cellulase or a combination of these. It is preferred to run the process near neutral pH, so it is preferred to use a cellulase with high activity in this pH range. In the past, cellulase preparations were generally produced by cultivation of naturally occurring microorganisms, and such preparations invariably contained a mixture of many different cellulase components. A process using such a mixed cellulase preparation is described in U.S. Pat. No. 4,832,864 (to Ecolab).

The rapid advances in recombinant DNA techniques have made it possible to produce single-component enzymes in high yield, and processes using single-component cellulases have therefore become more interesting. Thus, WO 91/17243 and WO 95/09225 (Novo Nordisk) describe a process using a single-component endoglucanase denoted EG V with a molecular weight of ~43 kD derived from *Humicola insolens* strain DSM 1800 with optimum activity near neutral pH. WO 94/21801 (Genencor) describes the use in "stone washing" of a single-component cellulase called EG III derived from *Trichoderma longibrachiatum* which is reported to have a pH optimum of 5.5–6.0 and to retain significant activity at alkaline pH. WO 95/16782 (Genencor International) suggests the use of other single-component cellulases derived from Trichoderma in "stone washing", but these cellulases are acidic and have virtually no activity at neutral pH.

A general problem in the known "stone washing" methods is that of back-staining, i.e. a phenomenon whereby dye already removed by abrasion deposits on parts of the fabric or garment so as to even out the desired variation of color density or to discolor any light-colored parts of the garment.

STATEMENT OF THE INVENTION

We have found that, surprisingly, the addition of a certain type of cellulase (hereinafter denoted as the first component) reduces back-staining. The cellulase in question has no significant abrading effect in itself.

Accordingly, the invention provides a method of forming localized variation of color density in the surface of a dyed cellulosic fabric, comprising agitating the fabric in an aqueous medium having a pH in the range 6.5–9 and containing:

a first component which is either
- (a) a cellulase of Family 5 which is able to hydrolyze cellotriose and/or p-nitrophenyl-b-1,4-cellobioside, or
- (b) a cellulase of Family 7, and a second component which is either
- (a) a mechanical abrading agent or
- (b) a cellulase having abrading activity, wherein each cellulase displays at least 30% of its maximum activity at pH 7.

Another aspect of the invention provides a composition for use in said method, comprising the above first and second components.

DEFINITIONS

In this specification with claims, the following definitions apply:

The term "cellulase" denotes an enzyme that contributes to the hydrolysis of cellulose, such a cellobiohydrolase (Enzyme Nomenclature E.C. 3.2.1.91), an endoglucanase (hereinafter abbreviated as "EG", E.C. 3.2.1.4), or a b-glucosidase (E.C. 3.2.1.21).

Cellulases are classified into families on the basis of amino-acid sequence similarities according to the classification system described in Henrissat, B. et al.: *Biochem. J.*, (1991), 280, p. 309–16, and Henrissat, B. et al.: *Biochem. J.*, (1993), 293, p. 781–788.

The cellulases used in this invention are preferably single components, i.e. the aqueous medium used in the invention should be free of other cellulase components than those specified. Single component enzymes can be prepared economically by recombinant DNA technology, i.e. they can be produced by cloning of a DNA sequence encoding the single component, subsequently transforming a suitable host cell with the DNA sequence and expressing the component in the host.

Accordingly, the DNA sequence encoding a useful cellulase may be isolated by a general method involving
- cloning, in suitable vectors, a DNA library e.g. from one of the microorganisms indicated later in this specification,
- transforming suitable yeast host cells with said vectors,
- culturing the host cells under suitable conditions to express any enzyme of interest encoded by a clone in the DNA library,
- screening for positive clones by determining any cellulase activity of the enzyme produced by such clones, and
- isolating the enzyme encoding DNA from such clones.

The general method is further disclosed in WO 94/14953 (Novo Nordisk) the contents of which are hereby incorporated by reference.

The DNA sequence coding for a useful cellulase may for instance be isolated by screening a cDNA library of the microorganism in question and selecting for clones expressing the appropriate enzyme activity (i.e. cellulase activity).

A DNA sequence coding for a homologous enzyme, i.e. an analogous DNA sequence, may be obtainable from other microorganisms. For instance, the DNA sequence may be derived by similarly screening a cDNA library of another fungus, such as a strain of an *Aspergillus sp.*, in particular a strain of *A. aculeatus* or *A. niger*, a strain of *Trichoderma sp.*, in particular a strain of *T. reesei, T. viride, T. longibrachiatum, T. harzianum* or *T. koningii* or a strain of a *Neocallimastix sp.*, a *Piromyces sp.*, a *Penicillium sp.*, an *Agaricus sp.*, or a *Phanerochaete sp.*

Alternatively, the DNA coding for a useful cellulase may, in accordance with well-known procedures, conveniently be isolated from DNA from a suitable source, such as any of the above mentioned organisms, by use of synthetic oligonucleotide probes prepared on the basis of a known DNA sequence.

The DNA sequence may subsequently be inserted into a recombinant expression vector. This may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

In the vector, the DNA sequence encoding the cellulase should be operably connected to a suitable promoter and terminator sequence. The promoter may be any DNA sequence which shows transcriptional activity in the host cell of choice and may be derived from genes encoding proteins either homologous or heterologous to the host cell. The procedures used to ligate the DNA sequences coding for the cellulase, the promoter and the terminator, respectively, and to insert them into suitable vectors are well known to persons skilled in the art (cf., for instance, Sambrook et al., Molecular Cloning. A Laboratory Manual, Cold Spring Harbor, N.Y., 1989).

The host cell which is transformed with the DNA sequence is preferably a eukaryotic cell, in particular a fungal cell such as a yeast or filamentous fungal cell. In particular, the cell may belong to a species of Aspergillus or Trichoderma, most preferably *Aspergillus oryzae* or *Aspergillus niger*. Fungal cells may be transformed by a process involving protoplast formation and transformation of the protoplast followed by regeneration of the cell wall in a manner known per se. The use of Aspergillus as a host microorganism is described in EP 238 023 (Novo Nordisk A/S), the contents of which are hereby incorporated by reference. The host cell may also be a yeast cell, e.g. a strain of Saccharomyces, in particular *Saccharomyces cerevisiae, Saccharomyces kluyveri* or *Saccharomyces uvarum*, a strain of *Schizosaccharomyces sp.*, such as *Schizosaccharomyces pombe*, a strain of *Hansenula sp., Pichia sp., Yarrowia sp.* such as *Yarrowia lipolytica*, or *Kluyveromyces sp.* such as *Kluyveromyces lactis.*

In the present context, the term "homologous" or "homologous sequence" is intended to indicate an amino acid sequence differing from those shown in each of the sequence listings shown hereinafter, respectively, by one or more amino acid residues. The homologous sequence may be one resulting from modification of an amino acid sequence shown in these listings, e.g. involving substitution of one or more amino acid residues at one or more different sites in the amino acid sequence, deletion of one or more amino acid residues at either or both ends of the enzyme or at one or more sites in the amino acid sequence, or insertion of one or more amino acid residues at one or more sites in the amino acid sequence.

However, as will be apparent to the skilled person, amino acid changes are preferably of a minor nature, that is conservative amino acid substitutions that do not significantly affect the folding or activity of the protein, small deletions, typically of one to about 30 amino acids; small amino- or carboxyl-terminal extensions, such as an amino-terminal methionine residue, a small linker peptide of up to about 20–25 residues, or a small extension that facilitates purification, such as a poly-histidine tract, an antigenic epitope or a binding domain. See in general Ford et al., Protein Expression and Purification 2: 95–107, 1991. Examples of conservative substitutions are within the group of basic amino acids (such as arginine, lysine, histidine), acidic amino acids (such as glutamic acid and aspartic acid), polar amino acids (such as glutamine and asparagine), hydrophobic amino acids (such as leucine, isoleucine, valine), aromatic amino acids (such as phenylalanine, tryptophan, tyrosine) and small amino acids (such as glycine, alanine, serine, threonine, methionine).

It will also be apparent to persons skilled in the art that such substitutions can be made outside the regions critical to the function of the molecule and still result in an active polypeptide. Amino acids essential to the activity of the polypeptide encoded by the DNA construct of the invention, and therefore preferably not subject to substitution, may be identified according to procedures known in the art, such as site-directed mutagenesis or alanine-scanning mutagenesis (Cunningham and Wells, Science 244, 1081–1085, 1989). In the latter technique mutations are introduced at every residue in the molecule, and the resultant mutant molecules are tested for biological (i.e. cellulase) activity to identify amino acid residues that are critical to the activity of the molecule. Sites of substrate-enzyme interaction can also be determined by analysis of crystal structure as determined by such techniques as nuclear magnetic resonance, crystallography or photoaffinity labeling. See, for example, de Vos et al., Science 255: 306–312, 1992; Smith et al., J. Mol. Biol. 224: 899–904, 1992; Wlodaver et al., FEBS Left. 309: 59–64, 1992.

The modification of the amino acid sequence may suitably be performed by modifying the DNA sequence encoding the enzyme, e.g. by site-directed or by random mutagenesis or a combination of these techniques in accordance with well-known procedures. Alternatively, the homologous sequence may be one of an enzyme derived from another origin than the cellulases corresponding to the amino acid sequences shown in each of the sequence listings shown hereinafter, respectively. Thus, "homologue" may e.g. indicate a polypeptide encoded by DNA which hybridizes to the same probe as the DNA coding for the cellulase with the amino acid sequence in question under certain specified conditions (such as presoaking in 5×SSC and prehybridising for 1 h at −40° C. in a solution of 20% formamide, 5×Denhardt's solution, 50 mM sodium phosphate, pH 6.8, and 50 mg of denatured sonicated calf thymus DNA, followed by hybridization in the same solution supplemented with 100 mM ATP for 18 h at −40° C.). The homologous sequence will normally exhibit a degree of homology (in terms of identity) of at least 50%, such as at least 60%, 65%, 70%, 75%, 80%, 85%, 90% or even 95% with the amino acid sequences shown in each of the sequence listings shown hereinafter, respectively.

The homology referred to above is determined as the degree of identity between the two sequences indicating a derivation of the first sequence from the second. The homology may suitably be determined by means of computer programs known in the art such as GAP provided in the GCG program package (Needleman, S. B. and Wunsch, C. D., *Journal of Molecular Biology,* 48: 443–453, 1970).

DETAILED DESCRIPTION OF THE INVENTION

Dyed cellulosic fabric

The process of the invention may be applied to any type of dyed cellulosic fabric where it is desired to form localized variation of color density in the surface. An example of particular commercial interest is denim, particularly indigo-dyed denim for use in blue jeans etc.

The fabric may be treated in the form of unsewn fabric or a sewn garment made of such fabric. It is of particular interest to apply the process of the invention to new, clean fabric or garment.

Component 1

The first component is a cellulase of Family 5 or 7 which displays at least 30% of its optimum activity at pH 7. It is present in an effective amount for preventing backstaining, typically 0.05–5 mg/l (as pure enzyme protein), particularly 0.1–0.5 mg/l; typically corresponding to an activity of 10–1000 ECU/I, particularly 100–1000 ECUII; or an activity of 0.5–100 ECUIg of fabric.

Family 5 cellulase

The Family 5 cellulase used in the invention is able to hydrolyze cellotriose and/or p-nitrophenyl-b-1,4-cellobioside (PNP-Cel); the cellulase may have an indirect action on cellotriose, hydrolyzing it to form cellobiose without any glucose formation. The ability of the cellulase to hydrolyze PNP-Cel can be determined by the assay method described below, and the cellulase is considered to meet this condition if this assay gives a result above 0.1 micromol of PNP per minute per ECU.

The Family 5 cellulase preferably does not have any cellulose binding domain. The Family 5 cellulase may be an alkaline cellulase (e.g. an endoglucanase) derived from a bacterial strain such as Bacillus or Clostridium.

One such Family 5 cellulase is the endoglucanase from Bacillus strain KSM-64 (FERM BP-2886). The cellulase and its amino acid sequence are described in JP-A 4-190793 (Kao) and Sumitomo et al., *Biosci. Biotech. Biochem.,* 56 (6), 872–877 (1992).

Another Family 5 cellulase is the endoglucanase from strain KSM-635 (FERM BP-1485). The cellulase and its amino acid sequence are described in JP-A 1-281090 (Kao), US 4,945,053 and Y. Ozaki et al., *Journal of General Microbiology,* 1990, vol. 136, page 1973–1979. It has an activity on PNP-Cel of 0.18 micromol PNP/min/ECU in the above assay.

A third Family 5 cellulase is the endoglucanase from strain 1139. The cellulase and its amino acid sequence are described in Fukumori F. et al., *J. Gen. Microbiol,* 132:2329–2335 (1986) and JP-A 62-232386 (Riken).

A fourth Family 5 cellulase is the endoglucanase Endo 3A from Bacillus lautus NCIMB 40250 described in WO 91/10732 (Novo Nordisk). The amino acid sequence described therein was later found to be incorrect, and the corrected sequence is shown in SEQ ID NO: 1. The cellulase has an activity on PNP-Cel of 0.44 micromol PNP/min/ECU.

A fifth Family 5 cellulase is the cellulase from *Bacillus sp.* NCIMB 40482 having an apparent molecular weight of approximately 45 kD, described in WO 94/01532 (Novo Nordisk). Its activity on PNP-Cel is 0.22 micromol PNP/min/ECU.

A sixth Family 5 cellulase is endoglucanase A from *Clostridium cellulolyticum* described in E. Faure et al., Gene, 84 (1), 39–46 (1989) and Fierobe H-P et al., J. Bacteriol., 173 (24), 7956–7962 (1991).

Family 7 cellulase

The Family 7 cellulase for use in the invention may be derived from a fungal strain and is typically able to hydrolyze cellotriose directly into cellobiose and glucose, and is able to hydrolyze PNP-Cel, as determined e.g. by the assay method described later.

The Family 7 cellulase may be derived from a strain of Humicola, preferably *H. insolens*. An example is endoglucanase EG 1 derived from *H. insolens* strain DSM 1800, described in WO 91/17244 (Novo Nordisk). The mature cellulase has a sequence of the 415 amino acids shown at positions 21–435 of FIG. 14 therein and has a specific activity of 200 ECU/mg (based on pure enzyme protein). This cellulase may further be truncated at the C-terminal by up to 18 amino acids to contain at least 397 amino acids. As examples, the cellulase may be truncated to 402, 406, 408 or 412 amino acids. Another example is a variant thereof denoted endoglucanase EG 1* described in WO 95/24471 (Novo Nordisk) and having a sequence of 402 amino acids shown in FIG. 3 therein.

Alternatively, the Family 7 cellulase may be derived from a strain of Myceliophthora, preferably *M. thermophila*, most preferably the strain CBS 117.65. An example is an endoglucanase described in WO 95124471 (Novo Nordisk) comprising the amino acids 21–420 and optionally also the amino acids 1–20 and/or 421–456 of the sequence shown in FIG. 6 therein.

As another alternative, the Family 7 cellulase may be derived from a strain of Fusarium, preferably *F. oxysporum*. An example is an endoglucanase derived from *F. oxysporum* described in WO 91/17244 (Novo Nordisk) and Sheppard, P. O. et al., Gene. 150:163–167, 1994. The correct amino acid sequence is given in the latter reference. This cellulase has a specific activity of 350 ECU/mg.

Component 2

The second component is a mechanical abrading agent and/or an abrading cellulase. A preferred embodiment of the invention uses a combination of a mechanical abrading agent and an abrading cellulase as the second component.

Examples of mechanical abrading agents are pumice, heat expanded perlite and abrading elements (e.g. abrading balls).

The abrading cellulase is one that exerts abrading or color clarification activity, e.g. as described in EP 220016 (Novo Nordisk A/S), and displays at least 30% of its optimum activity at pH 7. It may be a Family 12 or 45 cellulase having a cellulose binding domain.

A Family 45 cellulase for use in the invention may be derived from a strain of Humicola, preferably *H. insolens*. An example is an endoglucanase denoted EG V derived from *H. insolens* strain DSM 1800 having a molecular weight of ~43 kD. The cellulase and its amino acid sequence are described in WO 91/17243 (Novo Nordisk). It has a specific activity of 430 ECU/mg.

A Family 12 cellulase for use in the invention may be derived from a strain of Trichoderma, preferably *T. longibrachiatum*. An example is endoglucanase EG lll described in WO 94/21801 (Genencor) having the amino acid sequence shown therein.

The second component is present in an effective amount for abrasion to form localized variation of color density. If the second component is an abrading cellulase, it is typically present in an amount of 0.05–5 mg/l (as pure enzyme protein), particularly 0.1–0.5 mg/l; typically corresponding to an activity of 10–1000 ECU/I, particularly 100–1000 ECU/I; or an activity of 0.1–100 ECU/g of fabric, particularly 0.5–10 ECU/g.

Process conditions

The process of the invention may be carried out at conventional conditions in a washing machine conventionally used for stone-washing (e.g. a washer-extractor). Typical conditions are a temperature of 40–60° C. and a fabric: liquor ratio from 1:3 to 1:20 for 15 minutes to 2 hours. Optionally, conventional additives may be used, e.g. a buffer, a surfactant (anionic and/or non-ionic) and/or a polymer (such as PVP, polyacrylate and polyacrylamide).

Assay for Cellulase Activity

The cellulase endo-activity is determined by the reduction of viscosity of CMC (carboxy-methyl cellulose) in a vibration viscosimeter. 1 ECU (endo-cellulase unit) is the amount of activity which causes a 10-fold reduction of viscosity when incubated with 1 ml of a solution of 34.0 g/L of CMC (trade name Aqualon 7LFD) in 0.1 M phosphate buffer (pH 7.5), 40° C. for 30 minutes.

Assay for Hydrolysis of PNP-Cel

The ability of a cellulase to hydrolyze p-nitrophenyl-b-1, 4-cellobioside (PNP-Cel) is determined by steady-state kinetic, direct detection of the yellow color of the product p-nitrophenol (PNP) by absorption at 405 nm. The assay conditions are 37° C., pH 7.5 (0.1 M phosphate buffer). The hydrolysis rate (in micromol of PNP per minute) is compared to the cellulase activity (ECU), and the result is expressed as micromol PNP per minute per ECU.

EXAMPLES

Example 1

Indigo-dyed denim was treated together with white cotton swatches using various combinations of cellulase, as follows:

| | |
|---|---|
| pH | 7 (phosphate buffer in tap water) |
| Temperature | 55° C. |
| Equipment | Launderometer (150 ml containers) |
| Component 1 | EG I derived from *Humicola insolens* DSM 1800 0–2.3 ECU/ml as indicated below |
| Component 2 | EG V derived from *Humicola insolens* DSM 1800 0 or 0.27 ECU/ml |
| Denim | 5 g/container |
| White cotton | 2 swatches/container |
| Time | 2 hours |

After the treatment, lint was collected and measured as an expression of the abrading action of the cellulase(s). The remission of the white swatches after the treatment was measured (D R at 680 nm, relative to an experiment without any cellulase) and taken as an expression of back-staining. Results:

| | Component 1 ECU/ml | Component 2 ECU/ml | Abrasion (mg lint) | Back-staining reduction (D R) |
|---|---|---|---|---|
| Reference | 0 | 0 | — | 0 |
| | 0 | 0.27 | 33 | −3.8 |
| Invention | 0.115 | 0.27 | 42 | −0.7 |
| | 0.23 | 0.27 | 36 | 3.0 |
| | 1.15 | 0.27 | 38 | 8.2 |
| | 2.3 | 0.27 | 62 | 10.4 |

Good abrasion was obtained with the component 2 cellulase. The addition of the component 1 cellulase significantly reduced the back-staining.

Example 2

The following cellulases were tested at the same conditions as in Example 1:

Component 1 EG 1 or EG 1* derived from *Humicola insolens* DSM 1800 0, 0.67 or 1.33 ECU/ml Component 2 EG V derived from *Humicola insolens* DSM 1800, 0.7 ECU/ml Abrasion was evaluated by measuring the amount of lint after each treatment. Good abrasion was found in each experiment, with a slight increase by addition of EG 1 or EG 1*.

Back-staining inhibition was determined from the increase of absorbance of the filtrate at 680 nm and from the increase of remission of the white fabric at 420 nm. The results showed that essentially the same back-staining inhibition was obtained with EG 1 and EG 1*.

Example 3

In the first step, a blue-colored liquor from denim was prepared by shaking 12 pieces (5×5 cm) of blue denim with 800 ml of phosphate buffer (pH 7.0) and 0.8 ml non-ionic surfactant at 50° C. for 30 minutes, followed by filtration.

In the second step, 5 pieces of white cotton were incubated with 200 ml of the blue liquor at 50° C. for 30 minutes with 0–100 ECU/L of cellulase. The cellulase tested was a mixture of EG 1 derived from *Humicola insolens* DSM 1800 truncated to 406, 408 and 412 amino acids.

After rinsing and drying, the back-staining inhibition was determined from the increase f lightness (L*) of the white swatches as measured by Dr. Lange Micro Color Data Station. Results (average for 5 swatches):

| ECU/L | Average Lightness (L*) |
|---|---|
| 0 | 83.42 |
| 1 | 84.02 |
| 10 | 86.16 |
| 100 | 92.58 |

The results demonstrate that EG 1 is effective for reducing back-staining from blue denim onto white cotton.

Example 4

An alkaline Bacillus cellulase of Family 5 according to invention was tested in the same manner as in Example 3. The results were as follows:

| ECU/L | Lightness (L*) |
|---|---|
| 0 | 82.52 |
| 90 | 83.82 |

The results demonstrate that this cellulase is also effective in reducing back-staining.

Example 5

4 pieces (5×5 cm) of desized blue denim and 8 pieces (5×5 cm) of white mercerized cotton were agitated in 400 ml of 50 mM phosphate buffer (pH 7.0) containing a Family 5 or 7 cellulase together with a Family 45 cellulase according to the invention (200 ECU/l of each cellulase). After 30 minutes, the fabrics were rinsed under running tap water and air dried.

The Family 5 cellulase was an alkaline Bacillus cellulase. The Family 7 cellulase was EG 1 derived from *Humicola insolens* truncated to 408 amino acids. The Family 45 cellulase was EG V derived from *Humicola insolens* DSM 1800.

The lightness (L*) of the two fabrics and the absorbance at 680 nm of the supernatant were measured. Results:

| Cellulase family | | Lightness (L*) | | |
|---|---|---|---|---|
| First comp. | Second comp. | Mercerized cotton | Denim | $A_{680}$ |
| None | Family 45 | 84.8 | 22.83 | 0.132 |
| Family 7 | Family 45 | 86.3 | 23.55 | 0.212 |
| Family 5 | Family 45 | 86.2 | 23.50 | 0.238 |

The results for the mercerized cotton show increased lightness, i.e. reduced back-staining, by the addition of the second component cellulase according to the invention.

The results also show increased lightness, i.e. reduced back-staining, for the blue denim. A visual inspection showed the denim treated according to the invention had a more pronounced localized variation of color intensity, as desired.

The data for the absorbance of the supernatant show that more of the pigment remained in the liquid after the treatment.

We claim:

1. A method of forming localized variation of color density in the surface of a dyed cellulosic fabric, comprising agitating the fabric in an aqueous medium having a pH in the range 6.5–9 and containing:

a first component which is either (a) a cellulase of Family 5 which is able to hydrolyze p-nitrophenyl-β-1,4-cellobioside, or (b) a cellulase of Family 7, and a second component which is either (a) a mechanical abrading agent or (b) a cellulase having abrading activity, and which is different from said first component;

wherein each cellulase displays at least 30% of its maximum activity at pH 7.

2. The method of claim 1 wherein the fabric is indigo dyed denim.

3. The method of claim 1 wherein the first component is a cellulase of Family 5 without a cellulose binding domain derived from a bacterial strain.

4. The method of claim 3 wherein the Family 5 cellulase is derived from a Bacillus strain selected from the group consisting of *Bacillus sp.* KSM-64, 1139, KSM-635, NCIMB 40482, and *Bacillus lautus* NCIMB 40250, or is a cellulase having at least 60% homology with any of the foregoing.

5. The method of claim 1 wherein the first component is a cellulase of Family 7 derived from a fungal strain.

6. The method of claim 5 wherein the Family 7 cellulase is endoglucanase EG I derived from *H. insolens* strain DSM 1800, or is a cellulase having at least 60% homology with said EG I.

7. The method of claim 1 wherein the first component is present in an amount of 0.1–0.5 mg/l or at a concentration of 100–1000 ECU/l.

8. The method of claim 1 wherein the second component comprises both the mechanical abrading agent and the abrading cellulase.

9. The method of claim 1 wherein the second component is a cellulase of Family 45 having a cellulose binding domain and is derived from a fungal strain.

10. The method of claim 9 wherein the Family 45 cellulase is endoglucanase EG V derived from *H. insolens* strain DSM 1800, or is a cellulase having at least 60% homology with said EG V.

11. The method of claim 1 wherein essentially no cellulase other than the specified first and second component is present.

12. A cellulase composition comprising:

a first component which is either (a) a cellulase of Family 5 which is able to hydrolyze p-nitrophenyl-β-1,4-cellobioside, or (b) a cellulase of Family 7, and a second component which is either (a) a mechanical abrading agent or (b) a cellulase having abrading activity and which is different from said first component;

wherein each cellulase displays at least 30% of its maximum activity at pH 7 and wherein the composition can be used in an aqueous medium having a pH in the range of 6.5–9 for forming localized variation of color density in the surface of a dyed cellulosic fabric.

13. A method of forming localized variation of color density in the surface of a dyed cellulosic fabric, comprising agitating the fabric in an aqueous medium having a pH in the range 6.5–9 and containing:

(i) a first component which is either (a) a cellulase of Family 5 which is able to hydrolyze p-nitrophenyl-β-1,4-cellobioside, or (b) a cellulase of Family 7, and (ii) a second component which is a cellulase having abrading activity and which is different from said first component;

wherein each cellulase displays at least 30% of its maximum activity at pH 7.

14. The method of claim 13 wherein the second component is a cellulase of Family 45 having a cellulose binding domain and is derived from a fungal strain.

15. The method of claim 14 wherein the Family 45 cellulase is endoglucanase EG V derived from *H. insolens* strain DSM 1800 or is a cellulase having at least 60% homology with said EG V.

16. A cellulase composition comprising:

(i) a first component which is either (a) a cellulase of Family 5 which is able to hydrolyze p-nitrophenyl-β-1,4-cellobioside, or (b) a cellulase of Family 7, and (ii) a second component which is a cellulase having abrading activity and which is different from said first component;

wherein each cellulase displays at least 30% of its maximum activity at pH 7.

* * * * *